US006108483A

United States Patent [19]
Berkcan

[11] Patent Number: 6,108,483
[45] Date of Patent: Aug. 22, 2000

[54] ROTARY OPTICAL LINK USING A RADIATED WAVE IN A LOCALIZED AREA

[75] Inventor: Ertugrul Berkcan, Niskayuna, N.Y.

[73] Assignee: General Electric Company, Schenectady, N.Y.

[21] Appl. No.: 09/182,778

[22] Filed: Oct. 30, 1998

[51] Int. Cl.[7] ....................................................... A61B 1/00
[52] U.S. Cl. ........................................... 385/147; 128/922
[58] Field of Search .............................. 385/147; 128/922

[56] References Cited

U.S. PATENT DOCUMENTS

| | | | |
|---|---|---|---|
| 5,324,933 | 6/1994 | Berkcan | 250/227.23 |
| 5,767,200 | 6/1998 | Koike | 525/265 |
| 5,805,658 | 9/1998 | Hum et al. | 378/4 |
| 5,845,003 | 12/1998 | Hu et al. | 382/131 |

OTHER PUBLICATIONS

"Low–Loss Single–Mode Optical Waveguides and Efficient High–Speed Modulators of $LiNb_xTa_{1-x}O_3$ on $LiTaO_3$," A.M. Hunter, II, Applied Physics Letters, vol. 24, No. 11, Jun. 1974, pp. 545–547.

"An Electric Field Sensor Utilizing a Piezoelectric Polyvinylidene Fluoride ($PVF_2$) Film in a Single–Mode Fiber Interferometer," Kee P. Koo, IEEE Journal of Quantum Electronics, vol. Qe–18, No. 4, Apr. 1982, pp. 670–675.

"Optically Induced Refractive Index Changes in $BaTiO_3$," Journal of Applied Physics, vol. 41, No. 13, Dec. 1970, pp. 5188–5192.

"$Bi_4Ge_3O_{12}$:Cr: A New Photorefractive Material," E. Moya, L. Contreras, C. Zaldo, Journal Optical Society of America B, vol. 5, No. 8/Aug. 1988, pp. 1737–1741.

"Optically–Induced Refractive Index Inhomogeneities in $LiNbO_3$ and $LiTaO_3$," A. Ashkin, GD Boyd. JM Dziedzic, RG Smith, AA Ballman, JJ Levinstein, K. Nassau, Applied Physics Letters, vol. 9, No. 1, Jul. 1, 1966, pp. 72–74.

"Bragg Switch for Optical Channel Waveguides," B. Chen and CM Meijer, Applied Physics Letters, vol. 33, No. 1, Jul. 1, 1978, pp. 33–35.

Primary Examiner—John D. Lee
Assistant Examiner—Michelle R. Connelly-Cushwa
Attorney, Agent, or Firm—John F. Thompson; Jill M. Breedlove

[57] ABSTRACT

A computed tomography system employs an optical communications link to reliably transmit high bandwidth data from the gantry to the associated processor. The communications link comprises an optical emitter, an optical waveguide, an induced radiated wave chamber, and an optical detector. The optical emitter is attached to the gantry of the computed tomography system. The optical waveguide generates a total internal reflection breach in response to an electric field, light energy, magnetic energy, and alternatively, in response to heat produced within a induced radiated wave chamber. The optical emitter generates a high bandwidth optical data signal which travels along the optical waveguide in correspondence with data generated by the detector array on the gantry. An induced radiated wave chamber induces a breach in the total internal reflection condition in the portion of the waveguide disposed within the induced radiated wave chamber, to cause the high bandwidth optical data signal to be reflected from the waveguide within the induced radiated wave chamber and correspondingly not to be reflected outside the waveguide. The optical detector which is fixed to the induced radiated wave chamber detects data reflected from the optical data signal.

17 Claims, 9 Drawing Sheets

ROTARY OPTICAL LINK USING A RADIATED WAVE IN A LOCALIZED AREA

BACKGROUND OF THE INVENTION

The present invention relates to computerized tomography (CT) communication, and more particularly to a optical communication system employed in a CT system using electrical energy, light energy, a magnetic field, or thermal energy to change internal reflection conditions within a waveguide to cause a guided wave to be refracted so that high bandwidth data contained therein is radiated from the waveguide and detected by an optical detector within a localized area.

CT systems typically employ a rotating frame or gantry to obtain multiple x-ray images, or views, at different rotational angles. Each set of images is identified as a "slice." A patient or inanimate object is generally positioned in a central opening on the rotating frame on a table, the table being axially movable within the central opening so that the patient may be positioned at various locations enabling respective slices to be obtained at multiple axial positions. Each of the slices obtained is then processed in a computer to produce enhanced images that are useful for diagnoses and inspection.

The rotating frame includes an x-ray source, a detector array and electronics necessary to generate image data for each view. Stationary electronics is employed for processing raw image data. It is necessary to communicate image data between the rotating frame and a stationary frame of the CT system.

The rate of data communication between the stationary and rotating frames is important because it affects the speed at which the images can be processed. It is desirable to obtain image views as fast as possible to reduce patient discomfort and to maximize equipment utilization. In current CT systems, a single view typically comprises about 800 detector channels with a 16 bit representation for each individual detector channel (i.e., 12.8 thousand bits per view), and is typically repeated one thousand times per second, yielding a net data rate of approximately 13 million bits per second (Mbit/sec) for image data alone. Future CT systems capable of simultaneously constructing multiple image slices by employing four, eight, sixteen, or more times as many detector channels, will increase the data bandwidth requirement to the giga bits per second range.

Prior CT systems have employed brushes, slip rings, and radio frequency links for communicating the image data between the rotating frame and a stationary frame. CT systems utilizing brushes and slip rings for communications have generally suffered significant limitations in data transfer rates due to the substantial time required to propagate the signals around the circular slip rings. At the desired data rates, the electrical path length around the rings is an appreciable fraction of the data bit transfer period so that electromagnetic waves propagating around the rings in the opposite direction may arrive at the reception point at substantially different times within the bit transfer period causing signal interference.

Additionally, radio frequency communication links, historically, have not been able to achieve the data transfer rates in the giga-hertz range required of present and future CT systems. Radio frequency links typically operate in the Mega-hertz bandwidth because of radio frequency side band interference and electrical signal propagation limitations within the electronics which generate the radio frequency carrier signals. As such, it is desirable to employ a CT communications link between the stationary electronics and rotating electronics that can operate in the giga-hertz bandwidth so as to facilitate simultaneous image construction using a plurality of detector channels.

It is also desirable to provide a communication link between the stationary frame and the rotating frame which is immune to electromagnetic radiation interference such as is typically produced in a hospital environment by cellular telephones, defibrillating devices, surgical saws, and electrical noise produced by any given CT system.

SUMMARY OF THE INVENTION

The present invention provides a computed tomography system employing an optical communications link to reliably transmit high bandwidth data over the optical link. The communications link comprises an optical emitter, an optical waveguide, an induced radiated wave chamber, and an optical detector. The optical emitter is coupled to the gantry of the computed tomography system and extends along the length of the gantry. The optical waveguide generates a total internal reflection breach in response to energy applied to a portion of the waveguide. The optical emitter generates an optical data signal in correspondence with data generated within the gantry that travels along the optical waveguide. The induced radiated wave chamber generates the energy to which the waveguide responds, within the portion of the waveguide disposed within the induced radiated wave chamber, so as to cause the optical data signal to be refracted from the waveguide within the induced radiated wave chamber and, correspondingly, not be refracted outside the waveguide. The optical detector is coupled to the induced radiated wave chamber and is adapted to detect data refracted from the optical data signal.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

DETAILED DESCRIPTION OF THE INVENTION

Figure 1:
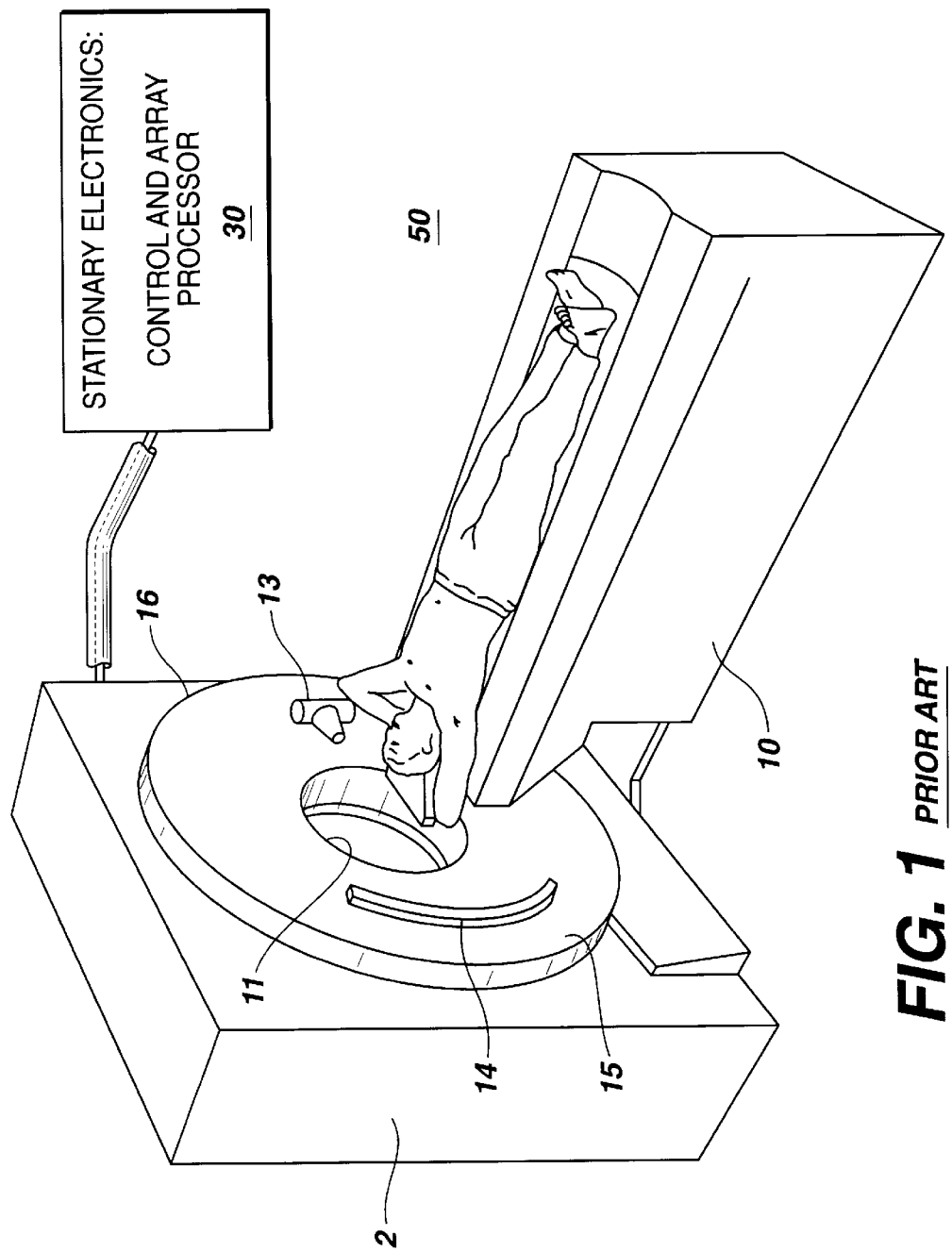
FIG. 1 is a prior art illustration of a computed tomography system having a gantry and stationary electronics.

A computed tomography (CT) system 50, illustrated in FIG. 1, typically employs a CT base 2, a source of imaging energy 13, a detector array 14, a annular rotating frame or gantry 15 having an outer circumference 16, and a stationary electronics system 30 comprising control electronics and array processor, to obtain multiple x-ray images of a patient or object. The patient or object is generally positioned in or near a central aperture 11 of gantry 15 on a table 10, which is axially movable along base 2, thus enabling respective x-ray slices to be obtained at multiple axial positions. Each of the slices obtained is then processed in a computer to produce enhanced images that are useful for diagnoses and inspection.

Figure 2:
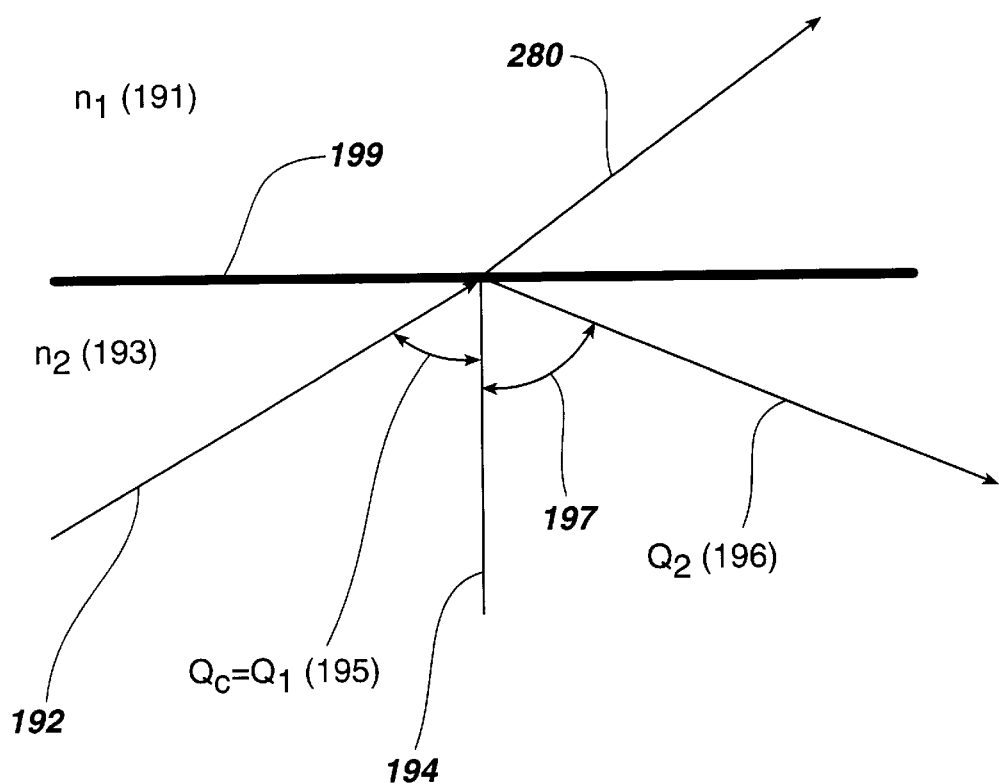
FIG. 2 is an optical illustration of the generation of an evanescent wave resulting from a TIR breach.

Total internal reflection (TIR) is the condition by which a guided wave within a waveguide is internally reflected within the waveguide. TIR is defined by Snell's law, and illustrated using the Law of refraction, $$n_1 \sin\theta_1 = n_2 \sin\theta_2 \qquad \text{equation 1}$$

where $\theta_1$ 195 is defined as the angle between the incident wave 192 and an axis 194 perpendicular to an axis 199 defining the interface between the two indices of refraction, where $\theta_2$ 197 is defined as the angle between a reflected wave 196 and axis 194 perpendicular to axis 199 defining the interface between the two indices of refraction, where $n_2$ 193 is defined as the index of refraction of the core material embodying incident wave 192 and reflected wave 196 which together comprise a guided wave 260 (FIG. 4), and where $n_1$ 191 is defined as the index of refraction of the material disposed adjacent to and in contact with the core material, as illustrated in FIG. 2.

The critical angle $\theta_c$ is defined as the angle above which the incident wave 192 is totally internally reflected, as illustrated by reflected wave 196 in FIG. 2. When the TIR condition is not met at least a portion of incident wave 192 is refracted from the core material, thus enabling a refracted wave 280 also referred to as evanescent wave 280 to be detected. The critical angle is determined by substituting 90 degrees for $\theta_2$ in equation 1 which yields, $$\sin\theta_c = n_1/n_2 \qquad \text{equation 2}$$

where, $\theta_c$ is the critical angle.

Figure 3:
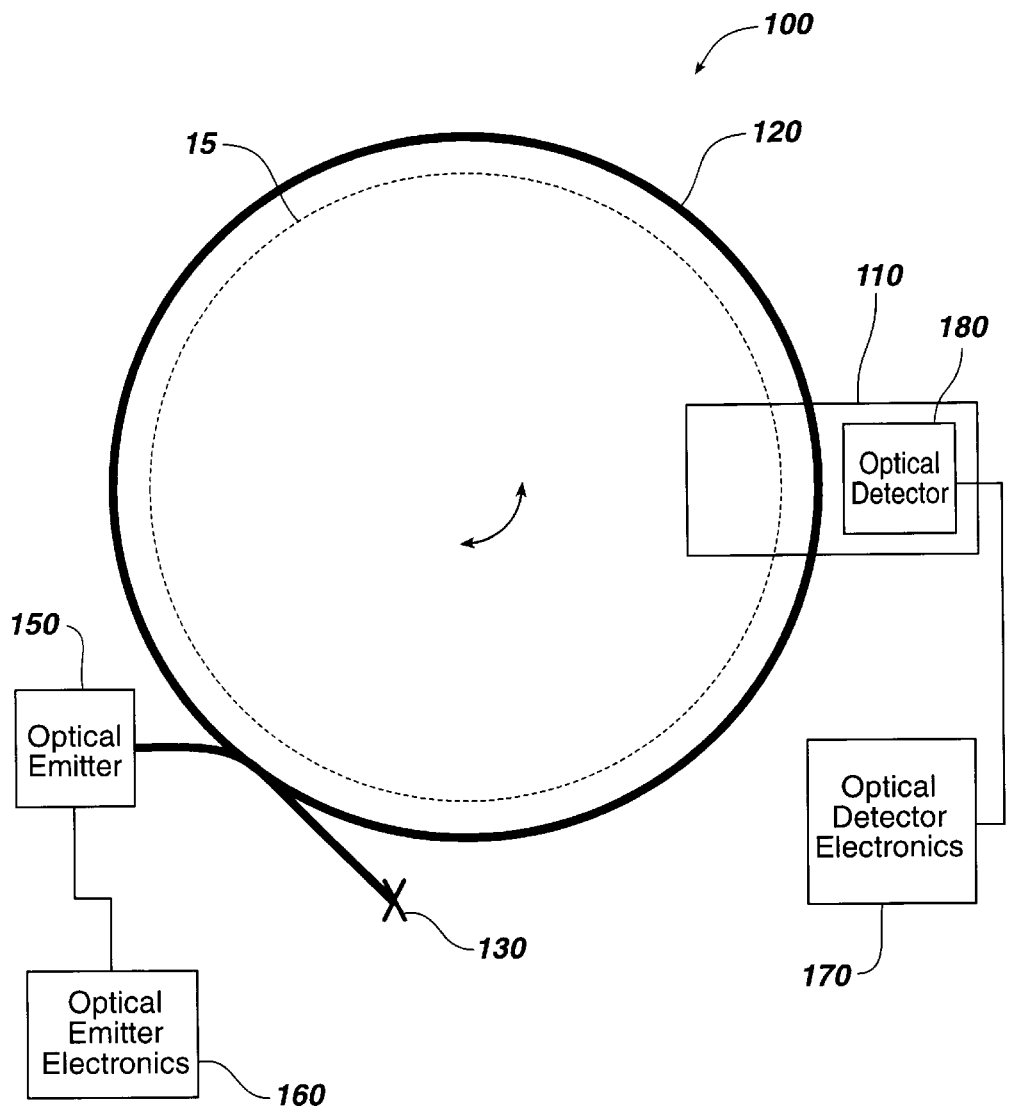
FIG. 3 is a functional block diagram of the communication link of the present invention coupled to the gantry of a computed tomography system.

CT system 50 (FIG. 1) is adapted to employ an optical communications link 100 to reliably transmit high bandwidth detector array data from gantry 15 to stationary electronics 30 by employing techniques to breach the TIR condition, as further illustrated in FIG. 3. In this specification, a breach in the TIR condition shall be referred to as a TIR breach. Optical communications link 100 is utilized to improve the data transmission rate by several orders of magnitude from the bandwidth of the typical communications link. For example the bandwidth of detector array data is increased in the present invention from about 13 mega-hertz, which is the bandwidth of the typical radio frequency communications link, to several giga-hertz, as is further discussed below. In this specification bandwidth is defined as the data transfer rate of signals generated by detector array 14. It is understood that detector array 14 comprises a plurality of detectors. For example, detector array 14 may comprise over one million detectors wherein the detectors are adapted to generate x-ray data that is used to simultaneously construct multiple CT image slices.

Figure 4:
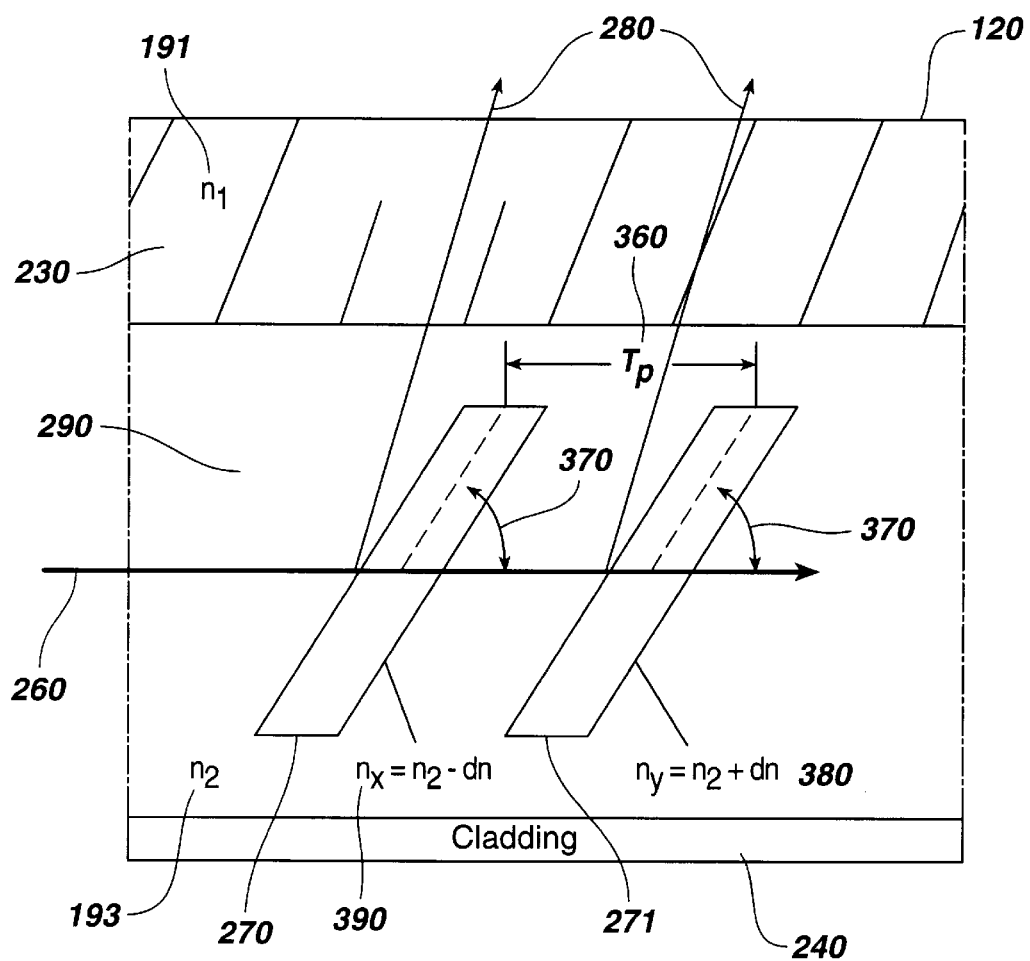
FIG. 4 is a block diagram illustration of the induced radiated wave chamber wherein gratings have been induced in the core of a waveguide section.

In an exemplary embodiment of the present invention, optical communications link 100 comprises: an optical emitter 150 which is coupled to optical emitter electronics 160; an optical waveguide 120 having a waveguide end 130; an induced radiated wave chamber 110; and an optical detector 180 which is coupled to optical detector electronics 170, as illustrated in FIG. 3. Optical waveguide 120 comprises waveguide core 290, reflective cladding 240, and also translucent cladding 230, as illustrated in FIG. 4.

Optical emitter 150 (FIG. 3) is adapted to generate a high bandwidth optical data signal in correspondence with data generated by detector array 14 (FIG. 1). The high bandwidth optical data signal is also identified as guided wave signal 260 (FIG. 4). The optical data signal generally has a wavelength of ($\lambda$) and travels along optical waveguide 120 and is reflected at waveguide end 130. Wavelength ($\lambda$) may typically be about 1300 nano-meters, and thus have a data bandwidth of about 1.2 giga-hertz. Alternatively, wavelength ($\lambda$) may be from about 1,000 to about 10,000 nano-meters to produce a bandwidth form about 1 to about 10 Giga-hertz. Wavelength ($\lambda$) is also chosen to minimize data signal dispersion in waveguide 120. Wavelength ($\lambda$) is selected to be above the critical frequency vector so that there is only a single guided wave mode and alternative a few guided wave modes as is commonly known in the art. (optical emitter 150 is mechanically coupled to optical waveguide 120. A gantry 15 rotates about the patient or object, optical emitter 150 correspondingly rotates with waveguide 120, as illustrated in FIG. 3.

Detector 180 is adapted to measure the evanescent wave 280 produced within induced radiated wave chamber 110. Detector 180 comprises for example, a silicon photo-diode which is selected to measure the wavelength of evanescent wave 280 and to generate a current that is proportional to evanescent wave 280. Alternatively, detector 180 comprises a Germanium photo-diode. Detector 180 is coupled to detector electronics 170, as illustrated in FIG. 3. Detector electronics 170 comprise, for example, an operational amplifier.

Numerous benefits result from the use of induced radiated wave chamber 120 to generate an evanescent wave only along that portion of waveguide 120 within induced radiated wave chamber 110. Total internal reflection enables guided wave 260 to be guided within the interior of waveguide 120 rather than being radiated out of waveguide 120, thereby maximizing the energy content of the data within guided wave 260. Also the signal to noise ratio of guided wave 260 is maximized because the amplitude of guided wave 260 is not degraded as it traverses along waveguide 120 because guided wave 260 is attenuated only within induced radiated wave chamber 120 and not along the portion of waveguide 120 not disposed within chamber 110. Total internal reflection is maintained for optical data signal and/or guided wave 260 within waveguide 120 for portions of waveguide 120 outside the induced radiated wave chamber 110. Additionally, waveguide 120 may be optically polarized. When waveguide 120 is polarized the dispersion of guided wave 260 is minimized because only the portion of guided wave 260 satisfying the polarization condition is internally reflected. Since signal dispersion is minimized the bandwidth of guided wave 260 may be maximized (i.e. a higher frequency data content of guided wave 260 may be utilized). For example, the bandwidth of the data content of guided wave 260 is improved by a factor of about ten because the dispersion is minimized in the present invention. Another contributing factor to the improved dispersion is the use of a smaller area detector 180 because of lower energy loss of guided wave 260 in the present invention.

Stationary induced radiated wave chamber 110 is used to change the conditions within a small portion of waveguide 120 by breaching the TIR condition so as to generate evanescent wave 280 which exits waveguide 120 within induced radiated wave chamber 110. Several techniques are employed in the generation of the evanescent wave 280 including, the use of gratings 270 and 271 in core 290 and translucent cladding 230 of waveguide 120, matching the index of core 290, modulating the index of translucent cladding 230, and changing the polarization of waveguide 120.

Generating Grating in the Core and Cladding

Figure 5:
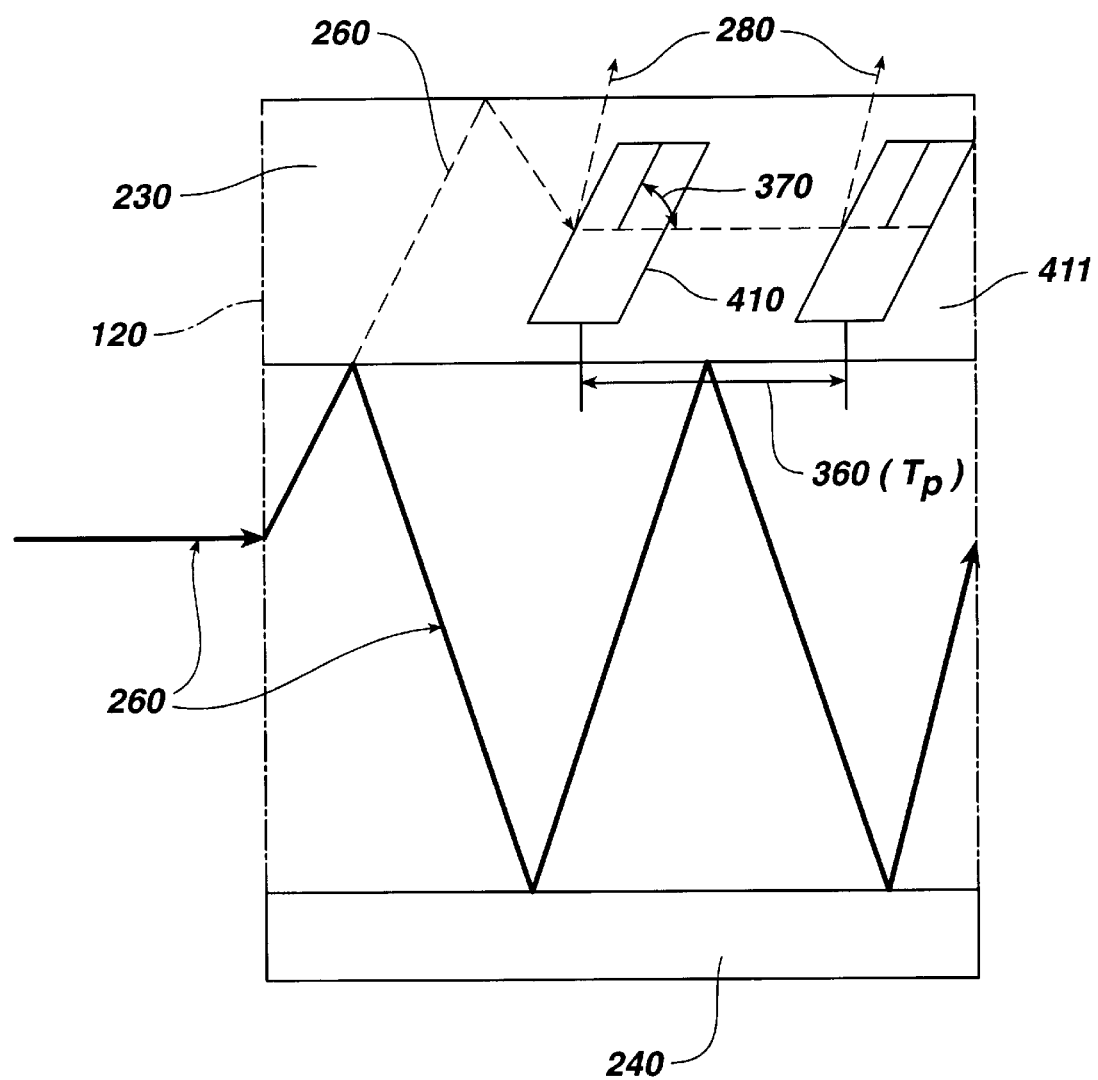
FIG. 5 is a block diagram illustration of the induced radiated wave chamber wherein gratings have been induced in the translucent cladding of a waveguide section.

Two techniques may be used to generate gratings 270 and 271 in core 290 and cladding 230 of waveguide 120, including, electric field response, and photo-refractive response. In each of these cases a period "Λ" (360) of the grating is chosen to satisfy the Bragg condition at the wavelength (λ) of guided wave 260, as illustrated in FIGS. 4 and 5. The Bragg condition is the set of circumstances where a plurality of gratings are generated within a material so as to deflect the guided wave, thereby satisfying conditions necessary to create a reflected or evanescent wave. Moreover, the Bragg condition defines an angle Θ (370) and period "Λ" (360), wherein a plurality of gratings 270 and 271 are set at angle (370) with respect to guided wave 260, and are spaced at distance or period "Λ" (360) apart from one another, to cause guided wave 260 (and hence the information content carried by guided wave 260) to exit waveguide 120 as evanescent wave 280. Note that a first grating 270 has an index of refraction defined by $n_x$ (390)= $n_2 - \Delta n_2$ and a next grating 271 has a index of refraction defined by $n_y$ (380)=$n_2 + \Delta n_2$. In a typical case were gratings 270 and 271 are generated there will be a plurality of gratings 270 and 271 generated. Gratings 270 and 271 cause guided wave 260 to be refracted in a new direction other than its original trajectory. The new trajectory of guided wave 260 is at an angle sufficient to satisfy the TIR breach condition, generating evanescent wave 280. Evanescent wave 280 exits waveguide 120 as described above. Evanescent wave 280 may then be detected by optical detector 180.

Evanescent wave 280 may also be generated in translucent waveguide cladding 230, as illustrated in FIG. 5. The material of translucent cladding 230 is adapted to propagate guided wave 260 as it is totally internally reflected by satisfying Snell's law as described above. By inducing cladding gratings 410 and 411 in translucent cladding 230 that satisfy the Bragg condition as discussed above evanescent wave 280 is generated.

Electric Field response

Figure 7:
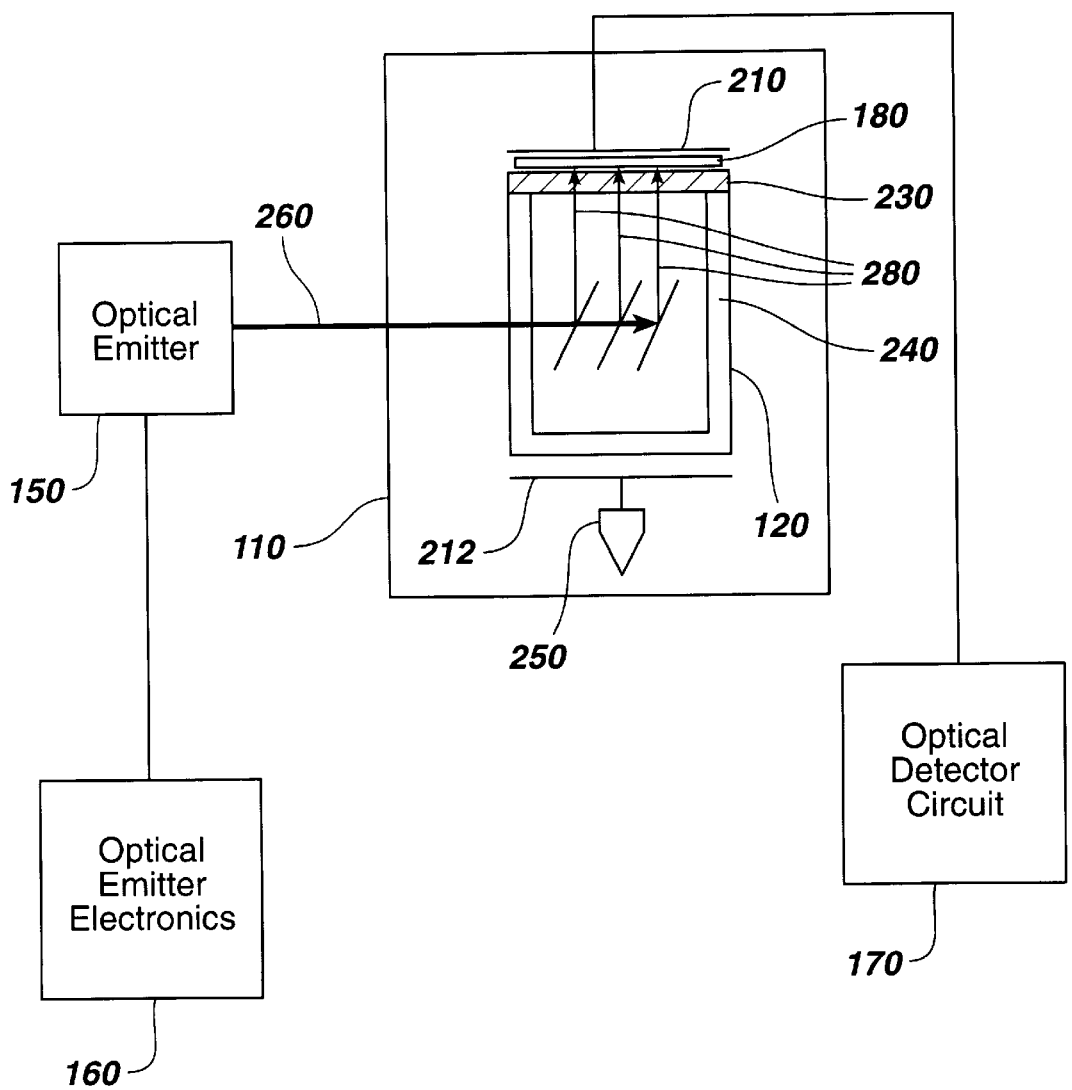
FIG. 7 is a schematic block diagram of the present invention where a TIR breach is induced in the waveguide by an electric field.

In one exemplary embodiment, waveguide 120 comprises an optical fiber coated with polyvinylidene fluoride ($PVF_2$) film so as to be responsive to an electrical field, as illustrated in FIG. 7. $PVF_2$ film has been demonstrated to operate to change the index of refraction in optical fibers, as discussed in the article, written by Kee P. Koo and G. H. Sigel, Jr., entitled, *An Electric Field Sensor Utilizing a Piezoelectric Polyvinylidene Fluoride ($PVF_2$) Film in a Single-Mode Fiber Intetferometer*, IEEE Journal of Quantum Electronics, Volume QE-18, No. 4, April 1982, pages 670–675, incorporated herein by reference. $PVF_2$ may be coated directly on waveguide 120 during fabrication, thus, enabling $PVF_2$ to stretch the optical fiber as $PVF_2$ imposes pressure on the periphery of the optical fiber, thus changing the density of the $PVF_2$ material and correspondingly the index of refraction of the $PVF_2$ material. Since $PVF_2$ is responsive to an electrical field, $PVF_2$ may be utilized so as to cause a TIR breach in waveguide 120.

An anode 210, a cathode 212, and a ground terminal 250 comprise components utilized to generate the electric field to which waveguide 120 is responsive, as illustrated in FIG. 7.

Photo-refractive Response

In another exemplary embodiment, waveguide 120 comprises an photo-refractive material such as Ti diffused $LiNbO_3$. For example, a fiber optic cable is disclosed for generating Bragg condition gradients wherein the fiber optic cable comprises Ti diffused $LiNbO_3$, in the article entitled, *Bragg switch for optical channel waveguides*, by B. Chen and C. M. Meijer, Appl. Phys. Lett. 33(1), 1 July 1978, published by the American Institute of Physics, incorporated herein by reference. This paper disclosed light beams that were deflected between two crossed channel waveguides using electro-optical phase gratings. In one example, the Bragg grating spacing or period "Λ" (360) was 4 micrometers, and the crossing angle Θ (370) for channels guides were 4 degrees, 6 minutes. The electro-magnetic wavelength of the light utilized was 6328 Angstroms.

Figure 8:
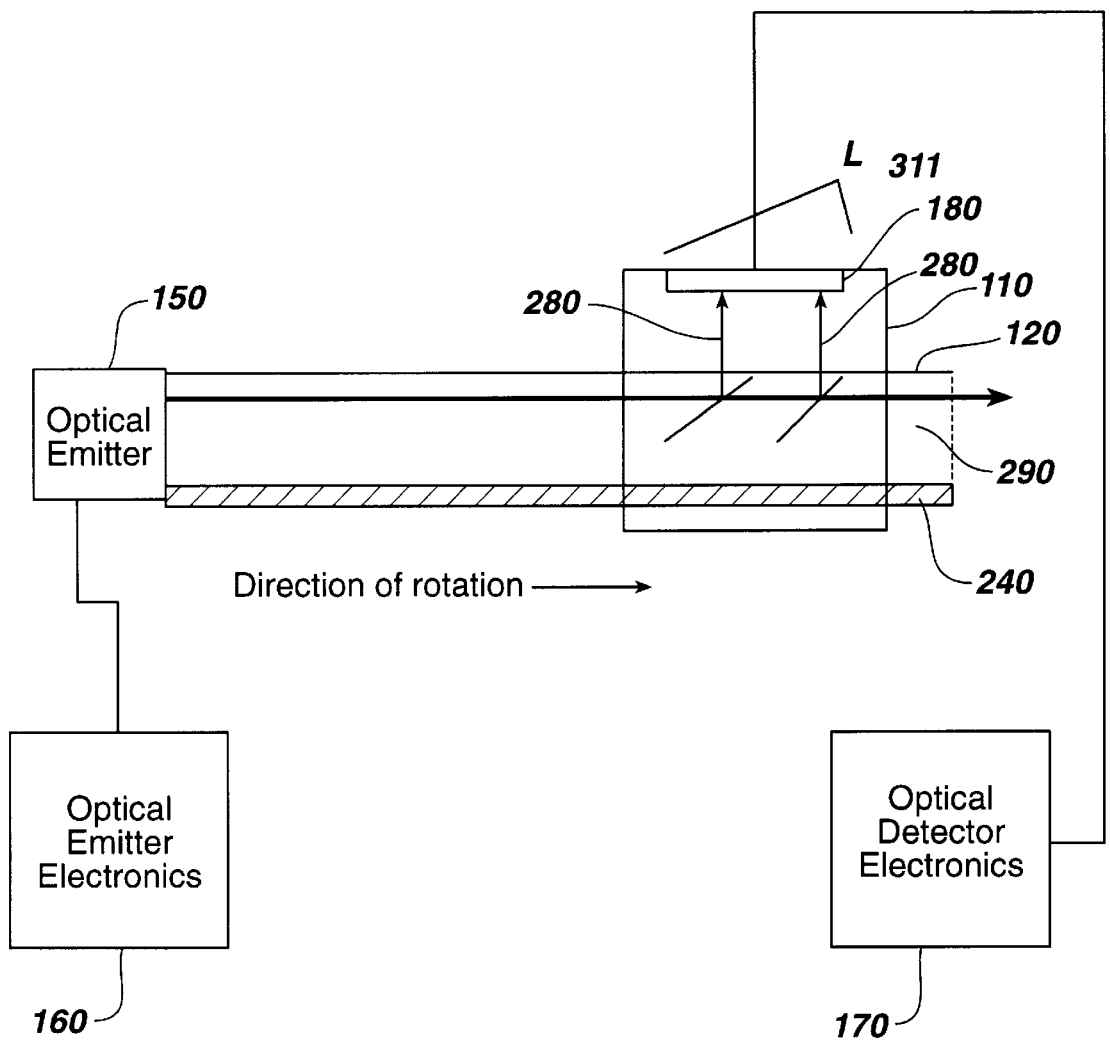
FIG. 8 is a schematic block diagram of the present invention where grating are induced in the waveguide by light energy.

FIG. 8, illustrates light energy 311 being generated in induced radiated wave chamber 110 and coupled to waveguide 120 to produce grating necessary to satisfy the Bragg condition.

Changing the Index of Refraction of the Core and Cladding

Thermal-refractive response

In another exemplary embodiment, waveguide 120 comprises thermally refractive material such as a transparent polymetric resin. For example, U.S. Pat. No. 5,767,200, incorporated herein by reference, describes a transparent polymetric resin that is responsive to heat energy so as to change the index of refraction of the transparent polymetric resin. Heat is defined as the increase in temperature of the portion of waveguide 120 within induced radiated wave chamber 110 with respect to the temperature of the portion of waveguide 120 outside induced radiated wave chamber 110. Typically, the increase in temperature required to change the index of refraction of the transparent polymetric resin is in a range from about 25 degrees Centigrade to about 45 degrees Centigrade.

Figure 6:
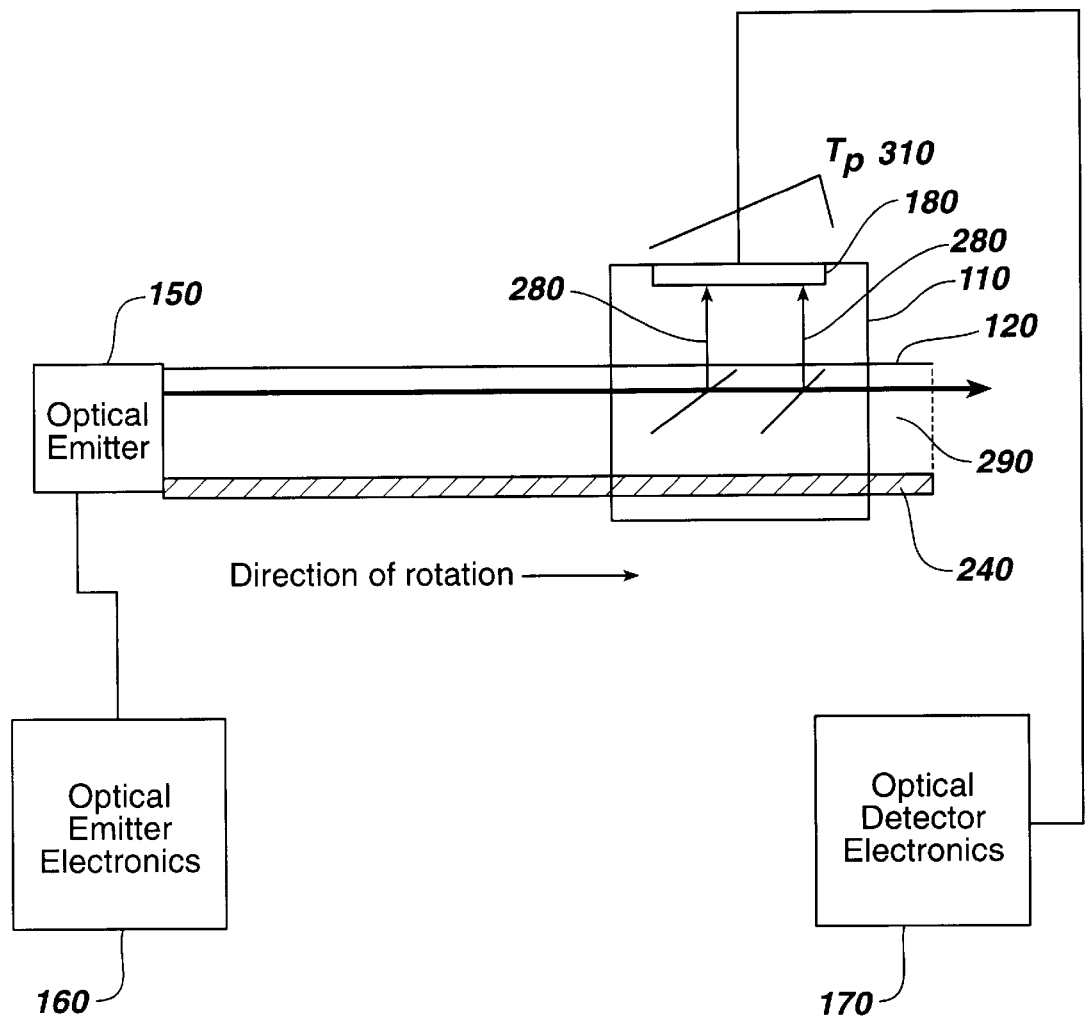
FIG. 6 is a schematic block diagram of the present invention where a TIR breach is induced in the waveguide by heat.

FIG. 6, illustrates heat energy 310 being generated in induced radiated wave chamber 110 and coupled to waveguide 120 to produce the change in TIR conditions necessary to generate evanescent wave 280.

Changing the Index of Refraction of the Cladding

In another exemplary embodiment, cladding 230 comprises liquid refractive material such as a transparent polymeric bath. In this embodiment, the index of refraction of $n_1$ is modified to generate a TIR breach in core 290 so as to cause evanescent wave 280 to be generated. The polymeric bath is selected so that the index of refraction of the polymeric bath 191 is changed to modify the critical angle 370 so as to create a TIR breach. The resulting evanescent wave 280 may then be detected by optical detector 180.

Modulating the Core and Cladding Grating

Induced radiated wave chamber 110 is adapted to generate a plurality of optical gratings which modulate in the portion of waveguide 120 disposed within induced radiated wave chamber 110 to cause the high bandwidth optical data signal to be refracted from waveguide 120 within induced radiated wave chamber 110 and correspondingly not be refracted outside waveguide 120, as discussed above. The generating of a modulated energy field in core 290 or cladding 230 is accomplished by generating gratings as described above, however, the energy is modulated so as to create modulating gratings. These gratings cause a TIR breach in waveguide 120, and subsequent evanescent wave 280. Optical detector 180 can then detect high bandwidth optical data associated with evanescent wave 280 that is produced from high bandwidth optical data signal and/or guided wave 260.

Polarization Refractive Response

Figure 9:
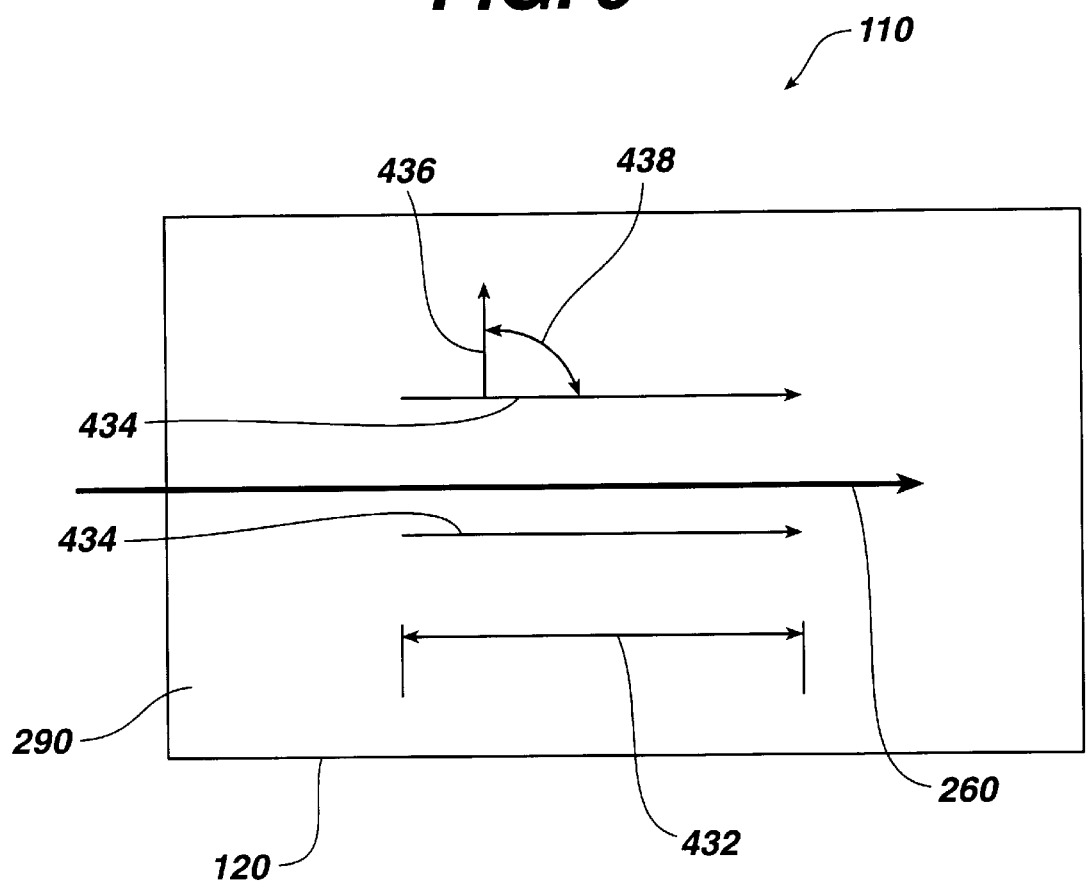
FIG. 9 is a block diagram of the present invention where a TIR breach is induced in the waveguide by a magnetic field.

In another exemplary embodiment, waveguide 120 comprises a polarization maintaining fiber using a material such as $GeO_2/SiO_2$ with $B_2O_3$ stress producing regions, whereby, a TIR breach is generated using a magnetically controlled change in the polarization vector. A guided wave 260 may be refracted from a polarization maintaining waveguide 120 when subjected to a polarization vector change on the guided wave 260. For example, the polarization change resulting from a magnetic field applied to waveguide 120 is defined by the line integral, commonly known as the Faraday effect, $$\Psi = \int \alpha V B \, dl \qquad \text{equation 3}$$

where "B" 434 is the magnetic field vector, "Ψ" 438 is the angle of rotation of the polarization vector 436 with respect to magnetic field vector 434, "α" 260 is guided wave vector, "V" is the Verdet constant of waveguide material 290, and "dl" 432 is the incremental length of waveguide 120 over which magnetic field vector 434 has influence, as illustrated in FIG. 9. Magnetic field vector 434 affects the total length of the induced radiated wave chamber 110, as such, the polarization of waveguide 120 may be changed within chamber 110. When polarization vector angle 438 is changed such that guided wave vector 260 does not satisfy TIR conditions, evanescent wave 280 is generated within chamber 110. Evanescent wave 280 may then be detected by optical detector 180.

Multi-mode Polarized Waveguide

Waveguide 120 is also adapted to accommodate a plurality of concurrent guided wave vectors 260, wherein each guided wave vector 260 has a unique wavelength. As such, a respective polarization vector 436 specifically tuned to generate a TIR breach in the associated guided wave vector 260 may be activated so that waveguide 120, having a plurality of guided wave vectors 260 concurrently internally reflected, may caused a predetermined respective evanescent wave 280 to be generated. A plurality of optical emitters 150 may be employed to generate each respective guided wave vector 260. Optical detector 180 is employed having a detection bandwidth sufficient to detect each respective evanescent wave 280. The effective bandwidth of communications link 100 is expanded when the above described multi-mode link 100 is employed to communicate data from detector array 14 to stationary electronics system 30.

Stationary Waveguide

In another exemplary embodiment of the present invention, optical emitter 150 is disposed inside waveguide 120. Waveguide 120 is stationary, and optical detector 180 and the induced radiated wave chamber 110 rotate along with gantry 15. The operation of communications link 100 is, however, the same as described above, in that as waveguide 120 passes through induced radiated wave chamber 110, a TIR breach is generated which causes evanescent wave 280 to be generated. Evanescent wave 280 is subsequently detected by detector 180.

The computed tomography system 50 is adapted to employ optical communications link 100 of the present invention to reliably transmit high bandwidth data from detector array 14 to stationary electronics 30 at a data transfer rate in the range from about one to about ten giga-hertz. Optical waveguide 120 responds to energy being applied to the portion of optical waveguide 120 within induced radiated wave chamber 110 so as to generate a TIR breach. Optical emitter 150 generates a high bandwidth optical data signal and/or guided wave 260 which travels within optical waveguide 120 in correspondence with data generated by detector array 14 on gantry 15. Induced radiated wave chamber 110 generates energy that causes the TIR within the portion of waveguide 120 disposed within induced radiated wave chamber 110 to cause evanescent wave 280, corresponding with high bandwidth optical data signal and/or guided wave 260, to be refracted from waveguide 120 within induced radiated wave chamber 110, and correspondingly not be refracted outside waveguide 120. Optical detector 180, which is coupled to induced radiated wave chamber 110 and coupled to stationary electronics 30, detects evanescent wave 280 and coupled data associated with evanescent wave 280.

It will be apparent to those skilled in the art that, while the invention has been illustrated and described herein in accordance with the patent statutes, modifications and changes may be made in the disclosed embodiments without departing from the true spirit and scope of the invention. It is, therefore, to be understood that the appended claims are intended to cover all such modifications and changes as fall within the true spirit of the invention.

What is claimed is:

1. A computed tomography system employing an optical communications link to reliably transmit optical data signals over said optical link, said computed tomography system having a rotating gantry and a detector array coupled to the gantry, said computed tomography system comprising:

an optical waveguide coupled to the gantry of said computed tomography system and extending along the length of the gantry, wherein said optical waveguide has optical properties that change in response to energy being applied to a portion of said optical waveguide; and an induced radiated wave chamber through which said optical waveguide is adapted to traverse, wherein said induced radiated wave chamber utilizes energy selected from the group including heat, light, a magnetic field, and a electric field, to generate a total internal reflection (TIR) breach within the portion of said waveguide disposed within said induced radiated wave chamber, so as to cause the optical data signal disposed within said optical waveguide to be radiated from the portion of said waveguide within said induced radiated wave chamber.

2. The computed tomography system as recited in claim 1, further comprising at least one optical emitter being coupled to said optical waveguide, wherein said at least one optical emitter generates a respective optical data signal in correspondence with data generated by the detector array on the gantry, and wherein the respective optical data signal travels within said optical waveguide.

3. The computed tomography system as recited in claim 2, wherein said at least one optical emitter generates a respective unique high bandwidth optical signal.

4. The computed tomography system as recited in claim 1, further comprising an optical detector being coupled to said induced radiated wave chamber, wherein said optical detector receives the respective radiated optical data signal.

5. The computed tomography system as recited in claim 1, wherein said computed tomography system is a magnetic resonance imaging system employing an optical communications link to reliably transmit high bandwidth data over said optical link.

6. The computed tomography system as recited in claim 1, wherein said optical waveguide is stationary.

7. The computed tomography system as recited in claim 6, wherein said induced radiated wave chamber is mechanically coupled to the gantry, and wherein said induced radiated wave chamber rotates therewith.

8. A computed tomography system employing an optical communications link to reliably transmit a high bandwidth optical data signal over said optical communications link, said computed tomography system having a rotating gantry and a detector array coupled to the gantry, said computed tomography system comprising:

an optical waveguide coupled to the gantry of said computed tomography system and extending along the length of the gantry, wherein said optical waveguide has optical properties that change in response to energy being applied to a portion of said optical waveguide;

an optical emitter coupled to said optical waveguide, wherein said optical emitter is adapted to generate the high bandwidth optical data signal in correspondence with data generated by the detector array on the gantry, and wherein the high bandwidth optical data signal is adapted to travel within said optical waveguide;

an induced radiated wave chamber through which said optical waveguide is adapted to traverse, wherein said induced radiated wave chamber is adapted to cause a TIR breach within the portion of said waveguide disposed within said induced radiated wave chamber, so as to cause the high bandwidth optical data signal to be radiated from said waveguide within said induced radiated wave chamber, and wherein the high bandwidth optical data signal is not radiated from said waveguide outside said induced radiated wave chamber; and an optical detector coupled to said induced radiated wave chamber, wherein said optical detector receives the radiated high bandwidth optical data signal.

9. The computed tomography system as recited in claim 8, wherein said induced radiated wave chamber utilizes energy selected from the group including heat, light, a magnetic field, and a electric field, to generate a TIR breach within the portion of said waveguide disposed within said induced radiated wave chamber, so as to cause the high bandwidth optical data signal to be radiated from the portion of said waveguide within said induced radiated wave chamber.

10. The computed tomography system as recited in claim 9, wherein said optical emitter is disposed inside said optical waveguide.

11. The computed tomography system as recited in claim 10, wherein said optical detector is mechanically coupled to said induced radiated wave chamber and rotates therewith.

12. The computed tomography system as recited in claim 8, wherein said optical waveguide is stationary.

13. The computed tomography system as recited in claim 12, wherein said induced radiated wave chamber is mechanically coupled to the gantry, and wherein said induced radiated wave chamber rotates therewith.

14. The computed tomography system as recited in claim 8, wherein said computed tomography system is a magnetic resonance imaging system employing an optical communications link to reliably transmit the high bandwidth optical data signal over the optical link.

15. A computed tomography system employing an optical communications link to reliably transmit high bandwidth data over said optical link, said computed tomography system having a rotating gantry and a detector array coupled to the gantry, said computed tomography system comprising:

means for generating at least one high bandwidth optical data signal;

an optical waveguide coupled to the gantry of said computed tomography system and extending along the length of the gantry, wherein said optical waveguide has optical properties that change in response to energy being applied to a portion of said optical waveguide;

an induced radiated wave chamber through which said optical waveguide traverses; and means for generating a TIR breach in the portion of said optical waveguide disposed within said induced radiated wave chamber, so as to cause said at least one high bandwidth optical data signal disposed within said optical waveguide to radiate from said optical waveguide into said induced radiated wave chamber.

16. The computed tomography system as recited in claim 15, further comprising means for detecting said at least one high bandwidth optical data signal radiated from said optical waveguide within said induced radiated wave chamber.

17. A computed tomography method employing an optical communications link to reliably transmit a high bandwidth optical data signal over said optical link, said computed tomography system having a rotating gantry and a detector array coupled to the gantry, said computed tomography system comprising the following steps:

means for generating the high bandwidth optical data signal within an optical waveguide;

means for generating a TIR breach in the high bandwidth optical data signal so as to cause the high bandwidth optical data signal to be radiated from the portion of said optical waveguide disposed within an induced radiated wave chamber; and means for detecting the radiated high bandwidth optical data signal.

* * * * *